(12) United States Patent
Green et al.

(10) Patent No.: US 10,409,958 B2
(45) Date of Patent: Sep. 10, 2019

(54) PROXIMITY-BASED PHARMACY APPLICATION SERVICES SYSTEM

(71) Applicant: MarkeTouch Media, Inc., Houston, TX (US)

(72) Inventors: Lyle M. Green, Pacific Palisades, CA (US); Charles E. Russo, Houston, TX (US); Randolph A. Rice, Austin, TX (US); Stephen M. Forrette, Houston, TX (US)

(73) Assignee: MarkeTouch Media, Inc., Houston, TX (US)

(*) Notice: Subject to any disclaimer, the term of this patent is extended or adjusted under 35 U.S.C. 154(b) by 519 days.

(21) Appl. No.: 15/008,426

(22) Filed: Jan. 27, 2016

(65) Prior Publication Data

US 2016/0217271 A1    Jul. 28, 2016

Related U.S. Application Data

(60) Provisional application No. 62/107,503, filed on Jan. 26, 2015.

(51) Int. Cl.
*G06F 19/00* (2018.01)
*G16H 10/65* (2018.01)

(52) U.S. Cl.
CPC ......... *G06F 19/3456* (2013.01); *G16H 10/65* (2018.01)

(58) Field of Classification Search
CPC ............. G06F 19/3456; G06F 19/3418; G06F 19/328; G06F 19/3475; G06F 19/326; G06F 19/00; G06Q 50/24; G06Q 30/0631; G06Q 30/0255; G06Q 10/087; G06Q 20/203; G16H 10/60
See application file for complete search history.

(56) References Cited

U.S. PATENT DOCUMENTS

| | | | |
|---|---|---|---|
| 8,762,175 B1* | 6/2014 | Shutko | G06Q 10/083 705/2 |
| 9,015,056 B2 | 4/2015 | Ditto | |
| 2012/0022944 A1 | 1/2012 | Volpi | |
| 2013/0218721 A1 | 8/2013 | Borhan et al. | |
| 2013/0254049 A1 | 9/2013 | Todd | |
| 2014/0089001 A1 | 3/2014 | Macoviak et al. | |
| 2015/0294084 A1* | 10/2015 | McCauley | G06F 19/3456 705/2 |

* cited by examiner

*Primary Examiner* — Maroun P Kanaan
(74) *Attorney, Agent, or Firm* — Holland & Hart LLP (57) ABSTRACT

Methods, systems, and devices for consumer interaction are described. An example method may include receiving, by a computing device, an indication that a mobile device associated with a first user account is located within a facility. The method may also include accessing, in response to the received indication, information from a pharmacy management software system associated with the first user account. The method may also include determining a refill opportunity associated with the first user account. Additionally, the method may include transmitting a refill opportunity notification to the mobile device based at least in part on the determined refill opportunity.

18 Claims, 9 Drawing Sheets

PROXIMITY-BASED PHARMACY APPLICATION SERVICES SYSTEM

CROSS REFERENCES

The present Application for Patent claims priority to U.S. Provisional Patent Application No. 62/107,502 by Green et al., entitled "Pharmacy Application Services System," filed Jan. 26, 2015, which is expressly incorporated by reference herein for all purposes.

BACKGROUND

Field of the Disclosure

The following relates generally to consumer systems, and more specifically to techniques for providing proximity-based pharmacy application services.

Description of the Related Art

Pharmacy systems are typically used in the delivery of pharmacy services. Pharmacy systems may manage producing medication administration records (MARs) and medication inventories as well as alerting users to drug-drug interactions, dose-range checking, and drug-allergy checking. Some pharmacy systems may track the dispensing history of patients' medication and information related to the patients' medication (e.g., prescribers' name and information, the date that the medication was prescribed and/or ordered, the number of doses or days prescribed, medication name, strength of medication, dose of medication, pharmacy location, pharmacist responsible for review and approval, and patient demographics). Some pharmacy systems may also include operational, financial, and data management functions, such as pharmacy billing, inventory management, and report generation for medication labels, fill lists, and patient profiles.

SUMMARY

The described features generally relate to one or more improved methods, systems, or devices that provide techniques for providing proximity-based pharmacy application services.

A method of consumer interaction is described. The method may include receiving, by a computing device, an indication that a mobile device associated with a first user account is located within a facility, accessing, in response to the received indication, information from a pharmacy management software system associated with the first user account, determining a refill opportunity associated with the first user account and transmitting a refill opportunity notification to the mobile device based at least in part on the determined refill opportunity.

An apparatus for consumer interaction is described. The apparatus may include means for receiving an indication that a mobile device associated with a first user account is located within a facility, means for accessing, in response to the received indication, information from a pharmacy management software system associated with the first user account, means for determining a refill opportunity associated with the first user account and means for transmitting a refill opportunity notification to the mobile device based at least in part on the determined refill opportunity.

A further apparatus is described. The apparatus may include a processor, memory in electronic communication with the processor, and instructions stored in the memory. The instructions may be operable to cause the processor to receive an indication that a mobile device associated with a first user account is located within a facility, access, in response to the received indication, information from a pharmacy management software system associated with the first user account, determine a refill opportunity associated with the first user account and transmit a refill opportunity notification to the mobile device based at least in part on the determined refill opportunity.

A non-transitory computer readable medium for consumer interaction is described. The non-transitory computer-readable medium may include instructions to cause a processor to receive an indication that a mobile device associated with a first user account is located within a facility, access, in response to the received indication, information from a pharmacy management software system associated with the first user account, determine a refill opportunity associated with the first user account and transmit a refill opportunity notification to the mobile device based on the determined refill opportunity.

Some examples of the method, apparatus, or non-transitory computer-readable medium described herein may further include processes, features, means, or instructions for determining the refill opportunity associated with the first user account comprises determining that the first user account has an available refill on an existing prescription.

Some examples of the method, apparatus, or non-transitory computer-readable medium described herein may further include processes, features, means, or instructions for determining the refill opportunity associated with the first user account comprises determining that a second user account has an available refill on an existing prescription, the second user account being linked to the first user account.

Some examples of the method, apparatus, or non-transitory computer-readable medium described herein may further include processes, features, means, or instructions for receiving a refill indication associated with the determined refill opportunity notification. Some examples of the method, apparatus, or non-transitory computer-readable medium described herein may further include processes, features, means, or instructions for providing for display information associated with the received refill indication and the determined refill opportunity.

Some examples of the method, apparatus, or non-transitory computer-readable medium described herein may further include processes, features, means, or instructions for transmitting a refill completion notification to the mobile device.

Some examples of the method, apparatus, or non-transitory computer-readable medium described herein may further include processes, features, means, or instructions for initiating an auto-payment process based on the received refill opportunity.

Some examples of the method, apparatus, or non-transitory computer-readable medium described herein may further include processes, features, means, or instructions for determining that the first user account qualifies for a medication therapy service based on the accessed information from the pharmacy management software system.

Some examples of the method, apparatus, or non-transitory computer-readable medium described herein may further include processes, features, means, or instructions for determining a disease state associated with the first user account based on the determined refill opportunity.

Some examples of the method, apparatus, or non-transitory computer-readable medium described herein may further include processes, features, means, or instructions for determining a service opportunity associated with the first user account based on the determined refill opportunity. Some examples of the method, apparatus, or non-transitory computer-readable medium described herein may further include processes, features, means, or instructions for transmitting a service opportunity notification to the mobile device.

DETAILED DESCRIPTION

In accordance with some aspects of the present disclosure, a pharmacy application services system and pharmacy application services mobile application associated with a mobile device may be integrated with proximity-based networking functions such as, but not limited to, iBeacons technology. In this regard, example aspect of the subject disclosure may include various communications technologies that enable the mobile device (e.g., a smart phone, tablet, or like device) to perform actions when in close proximity to a beacon transmitter/transceiver.

In accordance with some examples, a beacon transmitter/transceiver (e.g., an iBeacon, wireless access point, or similar technology) may be installed on one or both sides of any entry point into a facility (e.g., a store, building, drive-thru entrance, or other generally confined area). A consumer (or other user) may download the pharmacy application services mobile application onto his or her mobile device. When the consumer passes through the doors or other entry point, the pharmacy application services mobile application installed on the mobile phone detects the beacon transmitter/transceiver, and the pharmacy application services mobile application causes the mobile device to communicate with the pharmacy application services server. The pharmacy application services server may access a pharmacy management software system (as well as other patient and/or consumer management system) to determine whether the consumer associated with the mobile device has an active account on the pharmacy management software system.

When it is determined that the consumer associated with the mobile device has an active account, the pharmacy application services server may determine whether a prescription for the consumer is ready and available in a will call bin and/or whether a prescription for the consumer is available for refill, for example, by accessing the pharmacy management software system. In addition, the pharmacy application services server may determine whether the consumer qualifies for other services such as, but not limited to, Med Sync, Medication Therapy Management, screenings, immunizations, marketing messages, etc. For example, determining whether the consumer qualifies for other services may be based at least in part on a disease state of the consumer, a time of the year (e.g., Flu season), or other information associated with the patient or a particular product/service.

In some embodiments, the pharmacy application services server may provide notification to the mobile device that includes an actionable response. For example, an actionable response (e.g., delivery of a push notification—txt, rich text, html, etc.) may be sent to the mobile device based at least in part of a patient profile, patient record, marketing campaign, and/or available services. The pharmacy application services mobile application of the mobile device may allow the customer to respond to the push notifications. The pharmacy application services server, upon receiving a response from the mobile device, may cause information to be populated back into the pharmacy management system and/or other system associated with the particular push notification.

Aspects of the disclosure are initially described in the context of an example pharmacy application services system that includes one or more pharmacy application services servers. Aspects of the disclosure are further illustrated by and described with reference to device diagrams, system diagrams, and flowcharts that relate to techniques for providing proximity-based pharmacy application services via the pharmacy application services servers.

Figure 1:
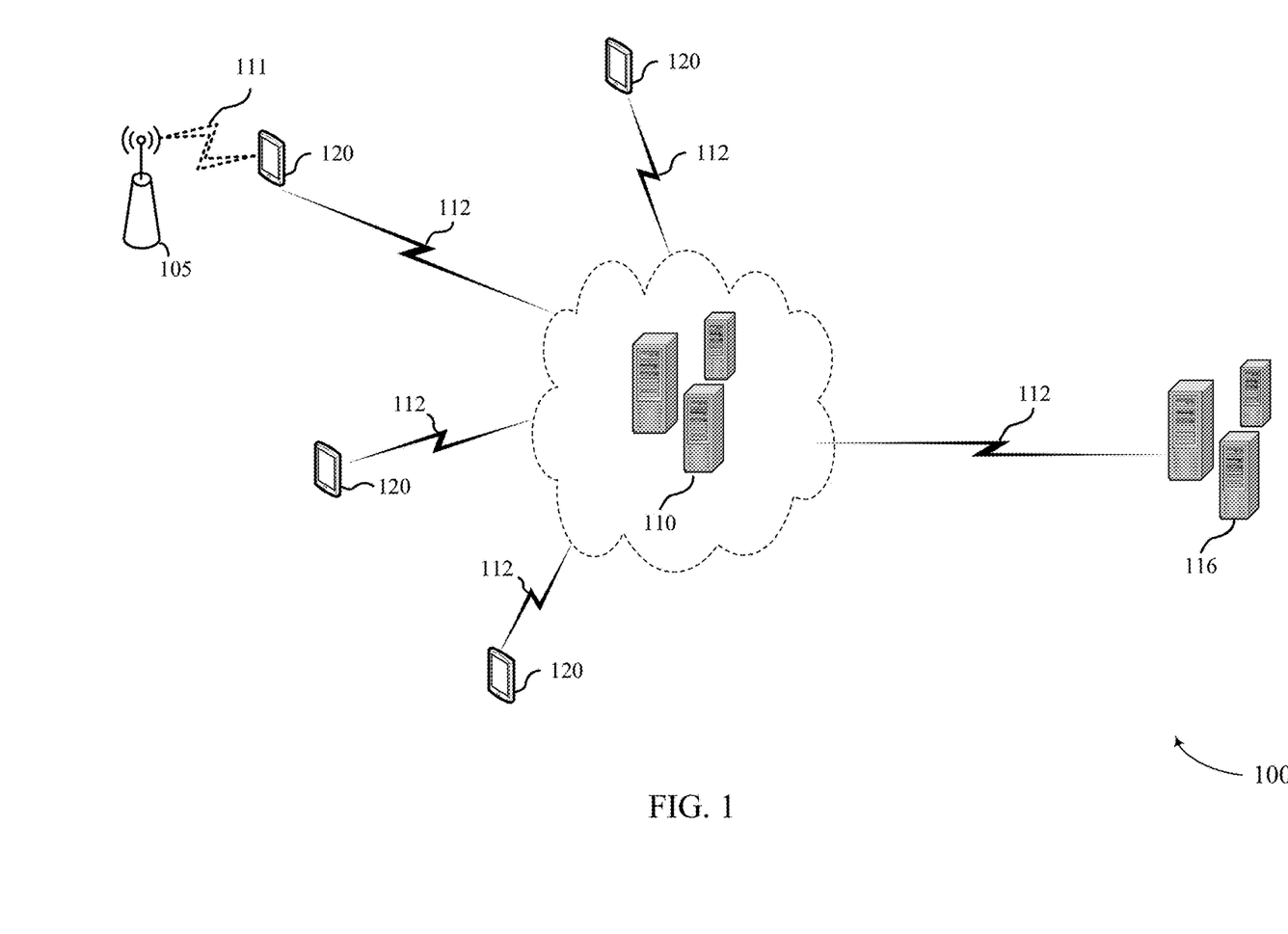
FIG. 1 illustrates an example of a pharmacy application services system in accordance with aspects of the present disclosure.

FIG. 1 illustrates an example of a pharmacy application services system 100 in accordance with various aspects of the present disclosure. In some examples, the pharmacy application services system 100 includes a beacon 105, one or more pharmacy application services servers 110, one or more pharmacy management servers 116, and mobile devices 120. The mobile devices 120 may communicate with the beacon 105 via a low-energy wireless communication 111. The one or more pharmacy application services servers 110 may communicate with the mobile devices 120 and the one or more pharmacy management servers 116 via communication links 112 (e.g., via a secure link in some implementations). The or more pharmacy application services servers 110 may also be in communication with the beacon 105. In some examples, the pharmacy application services system 100 (and the components and computing devices thereof) can be a hosted computing environment.

A pharmacy application services mobile application may installed on each mobile device 120. The pharmacy application services mobile application provides for communication with the one or more pharmacy application services servers 110. In accordance with some aspects, a mobile devices 120 may include control circuitry such as storage and processing circuitry. Storage and processing circuitry may include storage such as hard disk drive storage, non-volatile memory (e.g., flash memory or other electrically programmable read-only memory configured to form a solid state drive), volatile memory (e.g., static or dynamic random-access-memory), etc. In some aspects, processing circuitry in storage and processing circuitry may be used to control the operation of the mobile device. Such a processing circuitry may be based on one or more microprocessors, microcontrollers, digital signal processors, application specific integrated circuits, etc.

In some examples, the registration process for a mobile device 120 to register with the pharmacy application services system 100 includes downloading the pharmacy application services mobile application on to the mobile device 120. The user account associated with the mobile device 120 can fulfill a prescription through the pharmacy application services mobile application so that the pharmacy application services system 100 can acquire the necessary pharmacy account information to associate with the mobile device 120 and access information regarding the user account via the one or more pharmacy management servers 116.

In some cases, the user of the mobile device 120 can enter the pharmacy account information into the pharmacy application services mobile application on to the mobile device 120. For example, a user of a mobile device 120 may initiate a 'strong authentication' process without triggering a prescription order or refill. A 'strong authentication' process is used where protected health information (PHI) under Health Insurance Portability and Accountability Act (HIPAA) or the like is being provided to the user via mobile device 120. The 'strong authentication' process requires verification of some combination of first name, last name, date of birth, phone number, prescription/Rx number, residence zip code, and/or other information for verifying the user.

Thus, if the user has one or more prescriptions that are all enrolled in an auto-fill or Med Synch or a like appointment-based model in which prescriptions are synchronized to a monthly pickup date, that user can benefit from the pharmacy application services mobile application, for example, by being provided refill alerts based at least in part on proximity determinations or auto-payment options and/or other related services information associated with the prescriptions.

In this manner, the one or more pharmacy application services servers 110 can identify the registered mobile device 120 going forward and can perform proximity-based pharmacy application services when a proximity determination is made with respect to that registered mobile device 120. For example, a strong authentication process may be initiated by the one or more pharmacy application services servers 110 with a registered mobile device 120 to release medication information to the user of the registered mobile device 120 based at least in part on a proximity determination and subsequent proximity-based pharmacy application services performed.

The one or more pharmacy application services servers 110 may then provide medication information such as a prescription order history associated with the user account (e.g., the disclosure of PHI in some cases) to the registered mobile device 120 via the pharmacy application services mobile application installed thereon. It is to be appreciated that the one or more pharmacy application services servers 110 may accesses and operably communicate with other software systems such as, but not limited to, an interactive voice response (IVR), advisory alert systems, manufacturer subsidized program portals, healthcare portals, etc., the information from which may be provided to the registered mobile device 120.

In operation, the one or more pharmacy application services servers 110 may perform functions such as, but not limited to, determining any medications of user accounts available for pickup or refill, identifying any Medication Therapy Management opportunities associated with the user accounts, identifying potential disease states associated with the medications and other user account information, and determining screening, consults, immunization, and other healthcare opportunities for the users, and initiating quick pay and pickup for ready prescriptions. In carrying out these function, the one or more pharmacy application services servers 110 may communicate with the one or more pharmacy management servers 116 as well as other servers and/or computing devices.

In some examples, a proximity determination is made by the mobile device 120 receiving a signal (e.g., via low-energy wireless communication 111) from the beacon 105, and the mobile device 120 in association with the pharmacy application services mobile application initiates contact with the one or more pharmacy application services servers 110. The mobile device 120 may provide instantaneous location information to the one or more pharmacy application services servers 110 by transmitting information provided by the signal from the beacon 105, in accordance with some aspects.

In other examples, a proximity determination can be made by acquiring a unique identifier associated with the mobile device 120 from the beacon 105 (e.g., configured to receive wireless transmission such as but not limited to WiFi and Bluetooth transmissions from mobile devices 120). For example, a mobile device may have a mobile equipment identifier (MEID), an international mobile station equipment identity (IMEI), a Media Access Control (MAC) address, or the like that can be used to uniquely identify a particular mobile device. That unique identifier can then be provided to the one or more one or more pharmacy application services servers 110 by the beacon 105 to determine if that particular mobile device is registered with the pharmacy application services system 100. The one or more pharmacy application services servers 110 may initiate account information inquiries and contact with the particular mobile device 120 based at least in part on this proximity and device registration determination.

Figure 2:
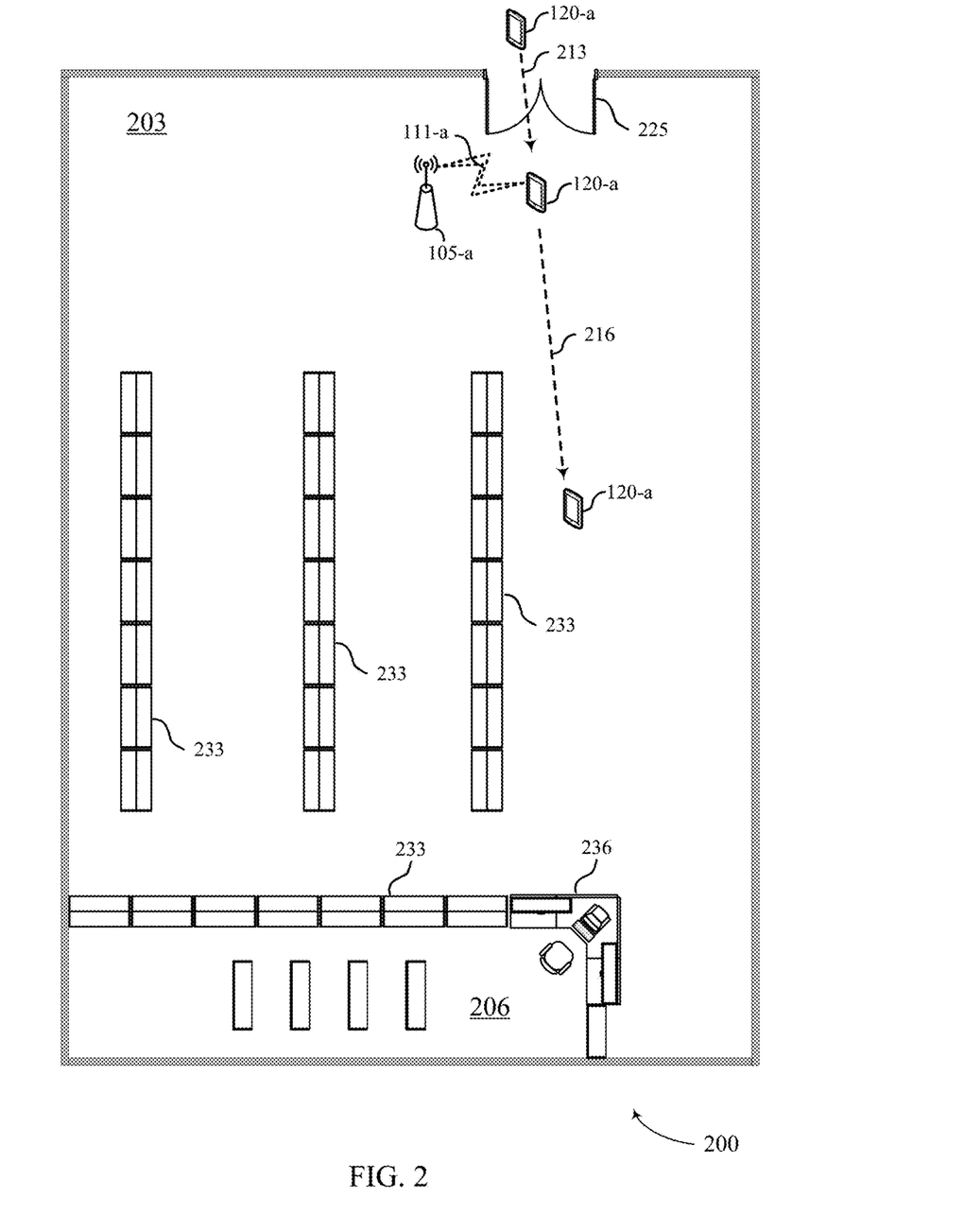
FIG. 2 illustrates an example of a system environment in which pharmacy application services techniques may be performed in accordance with aspects of the present disclosure.

FIG. 2 illustrates an example of a system environment 200 in which pharmacy application services techniques may be performed in accordance with aspects of the present disclosure. The system environment 200 includes a pharmacy application services system, such as the pharmacy application services system 100 described with reference to FIG. 1. A facility 203 may be equipped with a beacon 105-*a* (e.g., wireless transceiver, iBeacon, or similar technology) proximal to an entrance 225 of the facility 203. The facility 203 may be a retail store, grocery store, hospital, medical building, medical complex, or other generally confined area. In this regard, the facility 203 may include a plurality of shelves 233 to display products, for example, when facility 203 is a retail store or like setting. The facility 203 may include a pharmacy 206 or like prescription or medication processing and dispensing area. The pharmacy 206 can have a station 236 for ordering and picking up prescriptions.

A user (e.g., a consumer, pharmacy customer, etc.) may have download the pharmacy application services mobile application onto the mobile device 120-*a* and enters 213 the facility 203. When the user of the mobile device 120-*a* passes through the entrance 225, the pharmacy application services mobile application on the mobile device 120-*a* may detect a signal transmitted from the beacon 105-*a*. The pharmacy application services mobile application may cause the mobile device 105-*a* to communicate with the one or more pharmacy application services servers 110. The one or more pharmacy application services servers 110 may identify the user account associated with the mobile device 105-*a* and identify a location of the mobile device 120-*a* as being proximal to the facility 203. It is to be understood that, in various implementation, the one or more pharmacy application services servers 110 may be located outside of or within the premises of the facility 203.

The one or more pharmacy application services servers 110 may access one or more pharmacy management servers 116 (and/or in combination with other patient and/or consumer management systems) to determine whether the user associated with the mobile device 120-a is an active patient and may determine whether a prescription for the user is ready and available in a will call bin at station 236 and/or whether a prescription for the customer is available for refill. As such, the user may lose the convenience of taking care of these matters while in the facility 203, and the pharmacy 206 of the facility 203 may lose the potential revenue from additional sales of the refill medications, for example.

Additionally, the user of mobile device 120-a may not be able to make the user's presence and needs known until the user waits in line to talk to a pharmacist or pharmacy personnel at the station 236 of the pharmacy 206. In this regard, if the pharmacy application services system 100 can alert the pharmacist staff before the user of mobile device 120-a reaches the station 236 or without the user of mobile device 120-a ever having to go to the station 236, the user's prescription can potentially be prepared leading to greater efficiency and customer satisfaction.

In many cases, the user of mobile device 120-a may visit the facility 203, for example, when the facility 203 is a retail store or grocery store for a purpose not related to the pharmacy 206 (e.g., a typical shopping visit). The user of mobile device 105-a may not be aware that the user has one or more prescriptions available for refill or pickup. Additionally, according to some aspects, the pharmacy application services mobile application on the mobile device 120-a may include a link or association from the user's account in the pharmacy application services system 100 to one or more other user accounts (e.g., user accounts for the user's spouse, children, parents, other relatives, persons under the care of the user, etc.). Therefore, the user of mobile device 105-a may not be aware that the a family member has one or more prescriptions available for refill or pickup.

For example, the user of mobile device 120-a moves 216 toward certain shelves 233 to shop at the facility 203. The one or more pharmacy application services servers 110 may determines that the user account associated with the mobile device 120-a has a refill available for Prescription X associated with the user account and a refill available for Prescription Y associated with a different user account that is linked to the user account of the mobile device 120-a. The one or more pharmacy application services servers 110 transmits a notification of these two refill opportunities to the mobile device 120-a.

The user of mobile device 120-a receives the notification these refill opportunities based at least in part on the pharmacy application services mobile application (e.g., delivery of a push notification—txt, rich text, html, etc.) and respond via the mobile device 120-a. For example, the user of mobile device 120-a may decide to fulfill or process the refill of one or both of Prescription X and Prescription Y. The one or more pharmacy application services servers 110 receives the affirmative refill indication from the user of the mobile device 120-a and may initiate processes for fulfilling the refill order(s) (e.g., communicate with the one or more pharmacy management servers 116). In this manner, the one or more pharmacy application services servers 110 may provide display information regarding the refill order(s) to the station 236, for example, to alert the pharmacist or pharmacy personnel of the pharmacy 206 about the refill order(s). The display information regarding the refill order(s) may be from a display component of the one or more pharmacy application services servers 110, the one or more pharmacy management servers 116, and/or an associated patient and/or consumer management system.

The one or more pharmacy application services servers 110 and/or the pharmacy application services mobile application of the mobile device 120-a may provide an expected wait time for fulfilling the refill order(s). When the refill order(s) are completed, the one or more pharmacy application services servers 110 transmits a completion notification of the refill order(s) to the mobile device 120-a indicating that the refill order(s) are ready for pickup at the station 236. The one or more pharmacy application services servers 110 may also initiate an auto payment process for the completed refill order(s). For example, the pharmacy application services mobile application on the mobile device 120-a, the user account in the one or more pharmacy application services servers 110, or the user's pharmacy account in the one or more pharmacy management servers 116 may have a credit card on file and/or insurance card or information with which an auto payment and pickup process may be performed.

Moreover, pharmacists and pharmacy personnel typically do not have time to review a consumer or patient's profile for potential consultation, intervention opportunities, or the like that can improve patient health outcomes. Using the proximity awareness of the user of the mobile device 120-a, the pharmacy application services system 100, alone or in conjunction with the one or more pharmacy management servers 116 and/or an associated patient and/or consumer management system, can automatically provide such patient analysis and make that analysis available to the pharmacist so the pharmacist can use that information when the patient arrives at the station 236, for example. Additionally or alternatively, the pharmacy application services system 100 may transmit patient analysis information or recommendations to the mobile device 120-a. For example, such patient analysis information or recommendations may include providing a notification to the user of the mobile device 120-a including an interactive scheduling opportunity for a visit with a nurse practitioner collocated at the facility 203.

The one or more pharmacy application services servers 110 may determine whether the user of the mobile device 120-a qualifies for other services such as, but not limited to, Med Sync or Medication Therapy Management, and identify potential services or opportunities for the user of the mobile device 120-a. The one or more pharmacy application services servers 110 may also identify a potential disease state and determine possible screenings, consults, immunizations, marketing messages, other healthcare opportunities, and the like based at least in part on the identified disease state and/or other information, such as the refill order(s). For example, pharmacy application services system may determine that the customer qualifies for a Flu shot based at least in part on a particular time of year and that the customer had not year received a Flu shot for that year or specific time period. The pharmacy application services system may determine that the customer qualify for a promotional product based at least in part on current prescription or past history, for example, an offer for daily dose aspirin for a customer who has an active or recent statin prescription. Moreover, pharmacy application services system may initiate quick pay and pickup processes for ready prescriptions.

Figure 3:
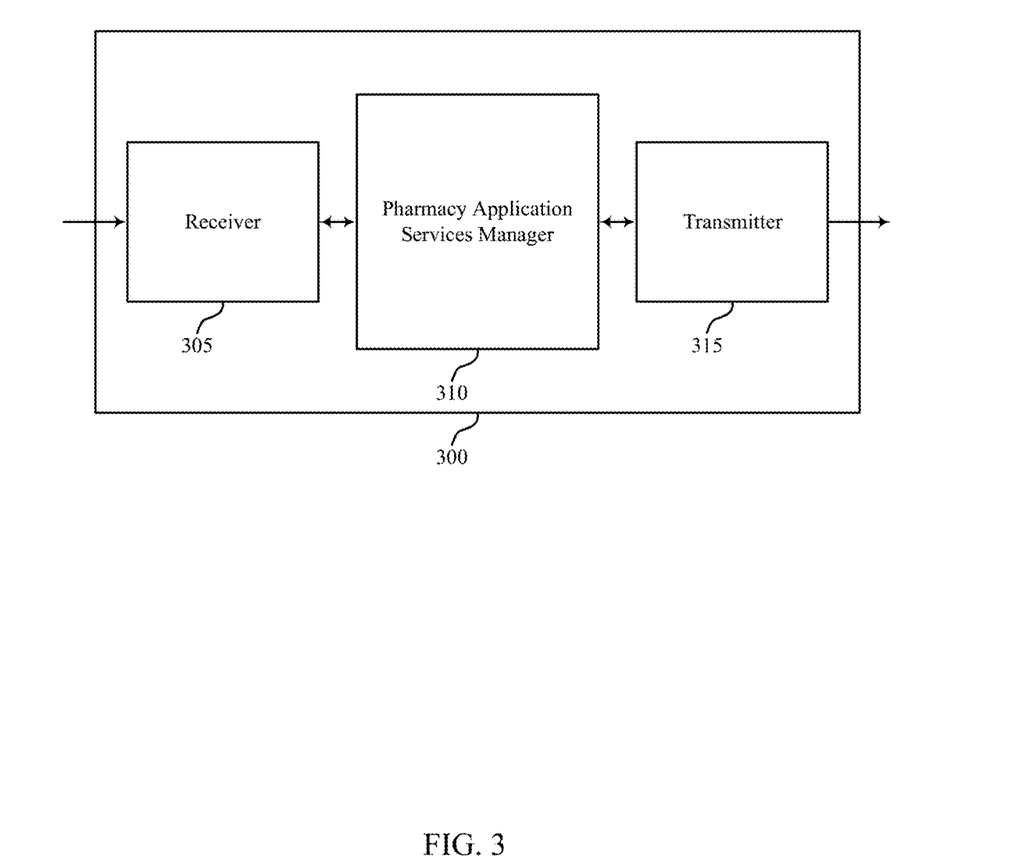
FIGS. 3 through 5 show block diagrams of examples of pharmacy application services servers that support techniques for providing proximity-based pharmacy application services in accordance with aspects of the present disclosure.

FIG. 3 shows a block diagram of a pharmacy application services server 300 that supports techniques for providing proximity-based pharmacy application services in accordance with various aspects of the present disclosure. Pharmacy application services server 300 may be an example of aspects of the one or more pharmacy application services servers 110 described with reference to FIGS. 1 and 2. Pharmacy application services server 300 may include receiver 305, pharmacy application services manager 310 and transmitter 315. Pharmacy application services server 300 may also include a processor. Each of these components may be in communication with each other.

The receiver 305 may receive information such as packets, user data, or control information associated with various information channels (e.g., control channels, data channels, and information related to proximity-based pharmacy application services, etc.). Information may be passed on to other components of the server or computing device. The receiver 305 may be an example of aspects of the transceiver 625 described with reference to FIG. 6.

The pharmacy application services manager 310 may receive an indication that a mobile device associated with a first user account is located within a facility, access, in response to the received indication, information from a pharmacy management software system associated with the first user account, determine a refill opportunity associated with the first user account, and transmit a refill opportunity notification to the mobile device based on the determined refill opportunity. The pharmacy application services manager 310 may also be an example of aspects of the pharmacy application services manager 605 described with reference to FIG. 6.

The transmitter 315 may transmit signals received from other components of pharmacy application services server 300. In some examples, the transmitter 315 may be collocated with a receiver in a transceiver module. For example, the transmitter 315 may be an example of aspects of the transceiver 625 described with reference to FIG. 6. The transmitter 315 may include one or more network links or interfaces.

Figure 4:
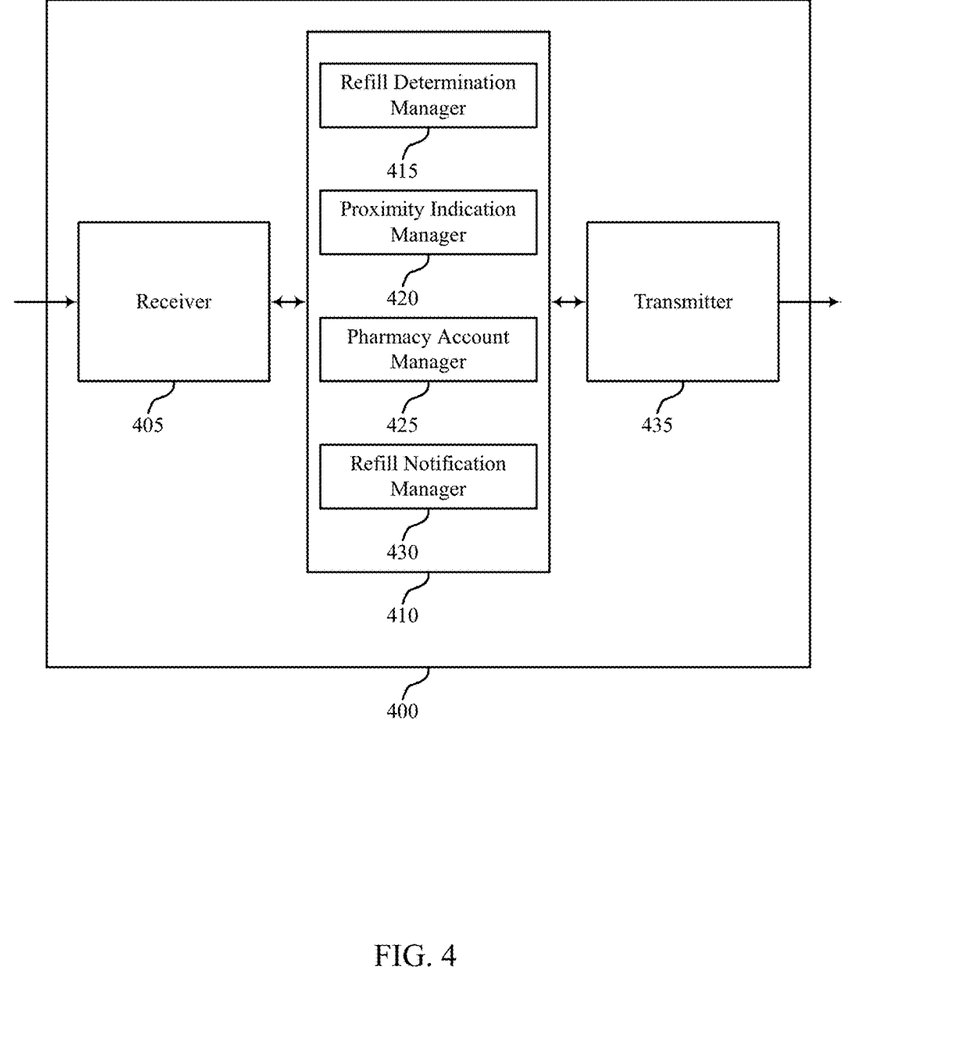

FIG. 4 shows a block diagram of a pharmacy application services server 400 that supports techniques for providing proximity-based pharmacy application services in accordance with various aspects of the present disclosure. Pharmacy application services server 400 may be an example of aspects of a pharmacy application services server 300 or one or more pharmacy application services servers 110 described with reference to FIGS. 1 through 3. Pharmacy application services server 400 may include receiver 405, pharmacy application services manager 410 and transmitter 435. Pharmacy application services server 400 may also include a processor. Each of these components may be in communication with each other.

The receiver 405 may receive information which may be passed on to other components of the server or computing device. The receiver 405 may also perform the functions described with reference to the receiver 305 of FIG. 3. The receiver 405 may be an example of aspects of the transceiver 625 described with reference to FIG. 6.

The pharmacy application services manager 410 may be an example of aspects of pharmacy application services manager 305 described with reference to FIG. 3. The pharmacy application services manager 410 may include refill determination manager 415, proximity indication manager 420, pharmacy account manager 425 and refill notification manager 430. The pharmacy application services manager 410 may be an example of aspects of the pharmacy application services manager 605 described with reference to FIG. 6.

The refill determination manager 415 may determine the refill opportunity associated with the first user account comprises determining that a second user account has an available refill on an existing prescription, receive a refill indication associated with the determined refill opportunity notification, determine a refill opportunity associated with the first user account, and determine the refill opportunity associated with the first user account comprises determining that the first user account has an available refill on an existing prescription.

The proximity indication manager 420 may receive an indication that a mobile device associated with a first user account is located within a facility. The pharmacy account manager 425 may provide for display information associated with the received refill indication and the determined refill opportunity, initiate an auto-payment process based on the received refill opportunity, and access, in response to the received indication, information from a pharmacy management software system associated with the first user account.

The refill notification manager 430 may transmit a refill completion notification to the mobile device, and transmit a refill opportunity notification to the mobile device based on the determined refill opportunity. The transmitter 435 may transmit signals received from other components of pharmacy application services server 400. In some examples, the transmitter 435 may be collocated with a receiver in a transceiver module. For example, the transmitter 435 may be an example of aspects of the transceiver 625 described with reference to FIG. 6. The transmitter 435 may utilize a single network link or interface, or it may utilize a plurality of network links or interfaces.

Figure 5:
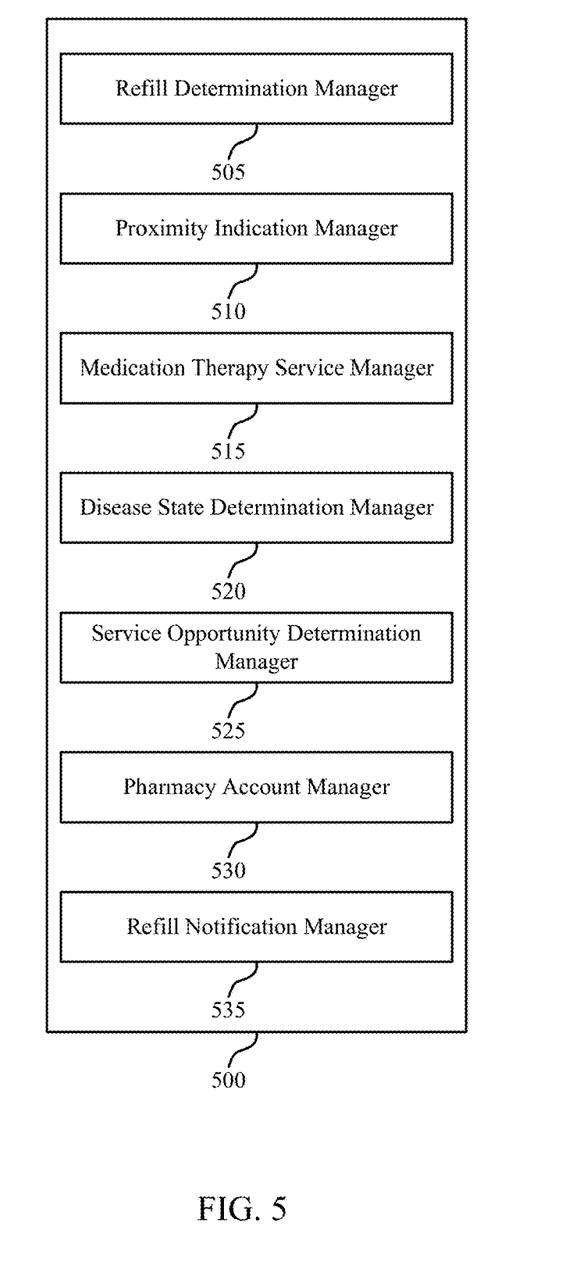

FIG. 5 shows a block diagram of a pharmacy application services manager 500 which may be an example of the corresponding component of pharmacy application services server 300 or pharmacy application services server 400. That is, pharmacy application services manager 500 may be an example of aspects of pharmacy application services manager 310 or pharmacy application services manager 410 described with reference to FIGS. 3 and 4. The pharmacy application services manager 500 may also be an example of aspects of the pharmacy application services manager 605 described with reference to FIG. 6.

The pharmacy application services manager 500 may include refill determination manager 505, proximity indication manager 510, medication therapy service manager 515, disease state determination manager 520, service opportunity determination manager 525, pharmacy account manager 530, and refill notification manager 535. Each of these modules may communicate, directly or indirectly, with one another (e.g., via one or more buses).

The refill determination manager 505 may determine the refill opportunity associated with the first user account comprises determining that a second user account has an available refill on an existing prescription, receive a refill indication associated with the determined refill opportunity notification, determine a refill opportunity associated with the first user account, and determine the refill opportunity associated with the first user account comprises determining that the first user account has an available refill on an existing prescription.

The proximity indication manager 510 may receive an indication that a mobile device associated with a first user account is located within a facility. The medication therapy service manager 515 may determine that the first user account qualifies for a medication therapy service based on the accessed information from the pharmacy management software system.

The disease state determination manager 520 may determine a disease state associated with the first user account based on the determined refill opportunity. The service opportunity determination manager 525 may determine a service opportunity associated with the first user account based on the determined refill opportunity, and transmit a service opportunity notification to the mobile device.

The pharmacy account manager 530 may provide for display information associated with the received refill indication and the determined refill opportunity, initiate an auto-payment process based on the received refill opportunity, and access, in response to the received indication, information from a pharmacy management software system associated with the first user account. The refill notification manager 535 may transmit a refill completion notification to the mobile device, and transmit a refill opportunity notification to the mobile device based on the determined refill opportunity.

Figure 6:
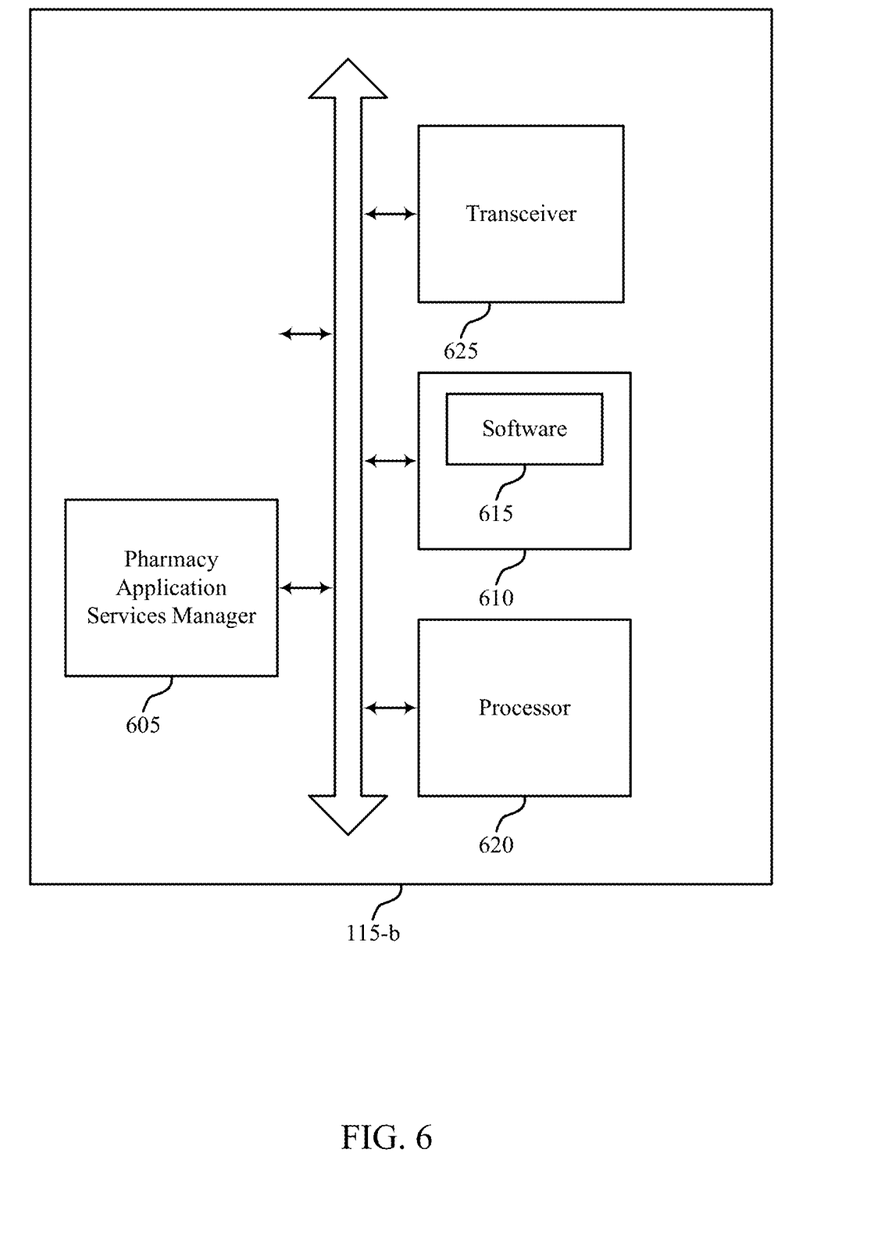
FIG. 6 illustrates a block diagram of an example of a system including a pharmacy application services server that supports techniques for providing proximity-based pharmacy application services in accordance with aspects of the present disclosure.

FIG. 6 illustrates a block diagram of an example of a pharmacy application services server 600 that supports techniques for providing proximity-based pharmacy application services in accordance with various aspects of the present disclosure. For example, pharmacy application services server 600 may be used in a consumer interaction system such as pharmacy application services system 100 as described with respect to FIG. 1. Pharmacy application services server 600 may be an example of one or more aspects of a pharmacy application services server 300, a pharmacy application services server 400, or a one or more pharmacy application services servers 110 as described with reference to FIGS. 1 through 5.

Pharmacy application services server 600 may also include pharmacy application services manager 605, memory 610, processor 620, and transceiver 625. Each of these modules may communicate, directly or indirectly, with one another (e.g., via one or more buses). The pharmacy application services manager 605 may be an example of a pharmacy application services manager as described with reference to FIGS. 3 through 5.

The memory 610 may include random access memory (RAM) and read only memory (ROM). The memory 610 may store computer-readable, computer-executable software including instructions that, when executed, cause the processor to perform various functions described herein. In some cases, the software 615 may not be directly executable by the processor but may cause a computer (e.g., when compiled and executed) to perform functions described herein. The processor 620 may include an intelligent hardware device, (e.g., a central processing unit (CPU), a microcontroller, an application specific integrated circuit (ASIC), etc.)

The transceiver 625 may communicate bi-directionally, via one or more network links or interfaces, wired, or wireless links, with one or more networks, as described herein. For example, the transceiver 625 may communicate bi-directionally via one or more network links or interfaces that may be optical, electrically wired, and/or wireless, with one or more other servers or networks, as described herein. The transceiver 625 may communicate bi-directionally with the one or more pharmacy management servers 116 and other servers that may aid in supporting the various proximity-based pharmacy application services described herein. The transceiver 625 may also communicate bi-directionally with the mobile devices 120. The transceiver 625 may also include a modem to modulate the packets and provide the modulated packets to the antennas for transmission, and to demodulate packets received from the one or more network links or interfaces.

Figure 7:
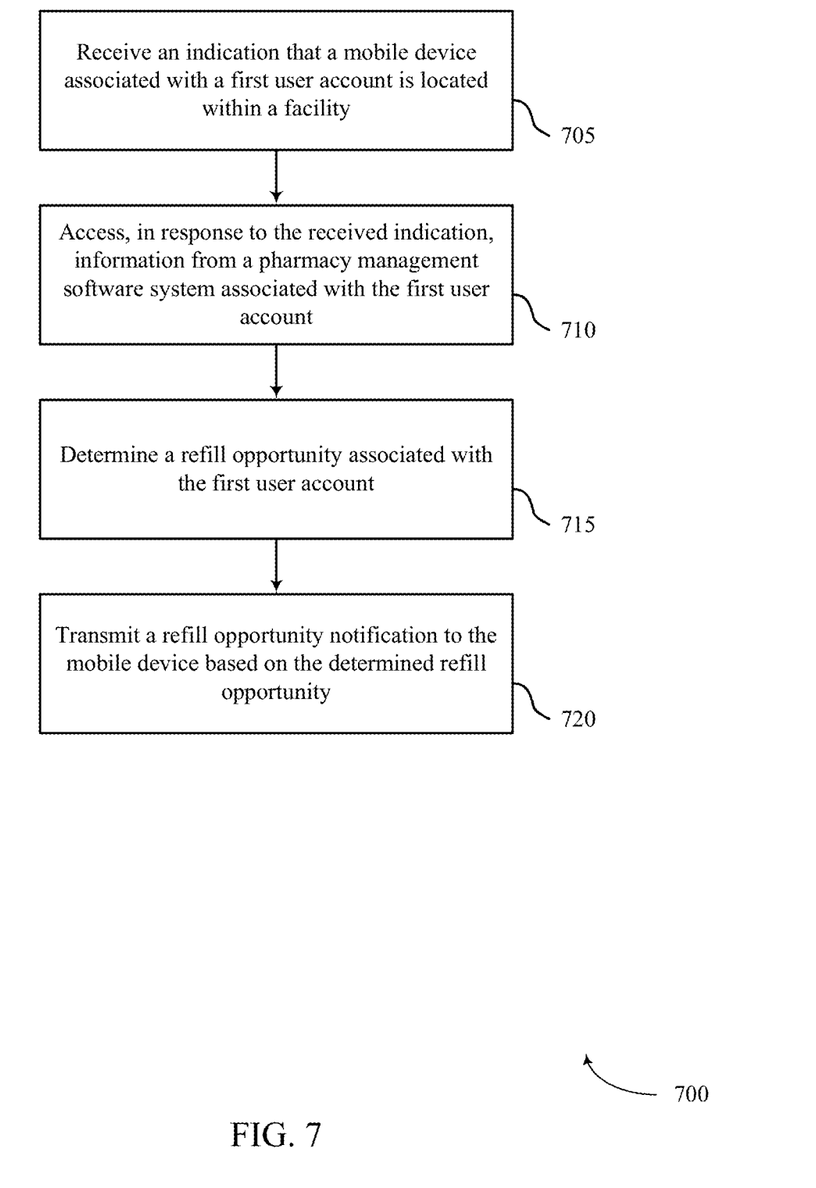
FIGS. 7 through 9 illustrate methods for providing proximity-based pharmacy application services in accordance with aspects of the present disclosure.

FIG. 7 shows a flowchart illustrating a method 700 for providing proximity-based pharmacy application services in accordance with various aspects of the present disclosure. The operations of method 700 may be implemented by a computing device (e.g., a server) such as pharmacy application services server 300, pharmacy application services server 400, pharmacy application services server 500, pharmacy application services server 600, or the one or more pharmacy application services servers 110 or its components as described with reference to FIGS. 1 through 6. In some examples, the computing device may execute a set of codes to control the functional elements of the computing device to perform the functions described below. Additionally or alternatively, the computing device may perform aspects the functions described below using special-purpose hardware.

At block 705, the computing device may receive an indication that a mobile device associated with a first user account is located within a facility as described herein with reference to FIGS. 1 through 6. In certain examples, the operations of block 705 may be performed by the proximity indication manager as described with reference to FIGS. 4 and 5.

At block 710, the computing device may access, in response to the received indication, information from a pharmacy management software system associated with the first user account as described herein with reference to FIGS. 1 through 6. In certain examples, the operations of block 710 may be performed by the pharmacy account manager as described with reference to FIGS. 4 and 5.

At block 715, the computing device may determine a refill opportunity associated with the first user account as described herein with reference to FIGS. 1 through 6. In certain examples, the operations of block 715 may be performed by the refill determination manager as described with reference to FIGS. 4 and 5.

At block 720, the computing device may transmit a refill opportunity notification to the mobile device based on the determined refill opportunity as described herein with reference to FIGS. 1 through 6. In certain examples, the operations of block 720 may be performed by the refill notification manager as described with reference to FIGS. 4 and 5.

Figure 8:
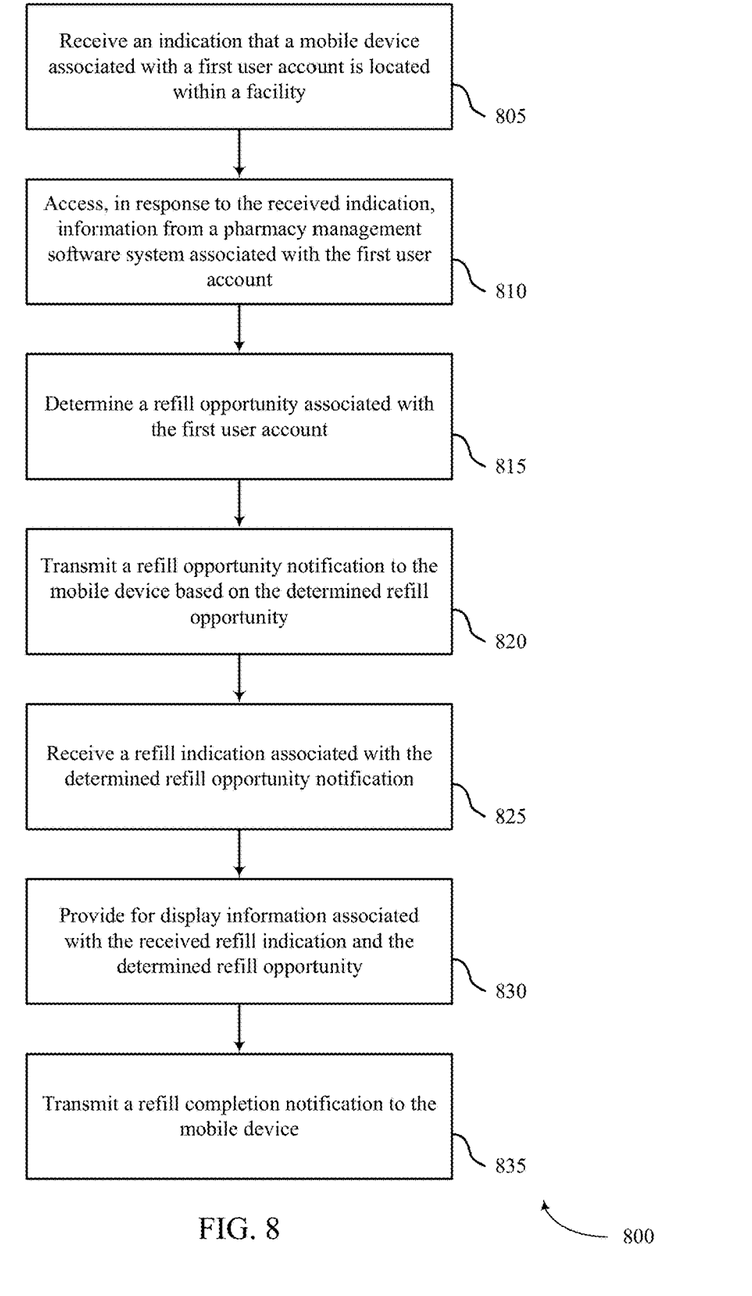

FIG. 8 shows a flowchart illustrating a method 800 for providing proximity-based pharmacy application services in accordance with various aspects of the present disclosure. The operations of method 800 may be implemented by a computing device (e.g., a server) such as pharmacy application services server 300, pharmacy application services server 400, pharmacy application services server 500, pharmacy application services server 600, or the one or more pharmacy application services servers 110 or its components as described with reference to FIGS. 1 through 6. In some examples, the computing device may execute a set of codes to control the functional elements of the computing device to perform the functions described below. Additionally or alternatively, the computing device may perform aspects the functions described below using special-purpose hardware.

At block 805, the computing device may receive an indication that a mobile device associated with a first user account (e.g., the owner of the mobile device) is located within a facility (e.g., a retail store) as described herein with reference to FIGS. 1 through 7. In certain examples, the operations of block 805 may be performed by the proximity indication manager as described with reference to FIGS. 4 and 5.

At block 810, the computing device may access, in response to the received indication (e.g., the indication can be from the mobile device or a beacon), information from a pharmacy management software system associated with the first user account as described herein with reference to FIGS.

1 through 7. In certain examples, the operations of block 810 may be performed by the pharmacy account manager as described with reference to FIGS. 4 and 5.

At block 815, the computing device may determine a refill opportunity (e.g., one or more prescriptions available to be refilled) associated with the first user account as described herein with reference to FIGS. 1 through 7. In some cases, the computing device may determine the refill opportunity associated with the first user account comprises determining that a second user account has an available refill on an existing prescription, where the second user account is linked to the first user account. In certain examples, the operations of block 815 may be performed by the refill determination manager as described with reference to FIGS. 4 and 5.

At block 820, the computing device may transmit a refill opportunity notification (e.g., a push notification indicating the availability of the one or more prescriptions to be refilled) to the mobile device based on the determined refill opportunity as described herein with reference to FIGS. 1 through 7. In certain examples, the operations of block 820 may be performed by the refill notification manager as described with reference to FIGS. 4 and 5.

At block 825, the computing device may receive a refill indication (e.g., an affirmative response back from the mobile device that the user wishes fulfill or process the one or more prescriptions available to be refilled, or a decline response regarding the one or more prescriptions available to be refilled) associated with the determined refill opportunity notification as described herein with reference to FIGS. 1 through 7. In certain examples, the operations of block 825 may be performed by the refill determination manager as described with reference to FIGS. 4 and 5.

At block 830, the computing device may provide for display (e.g., via a monitor or display screen associated with the computing device or an associated computing device) information associated with the received refill indication and the determined refill opportunity as described herein with reference to FIGS. 1 through 7. In certain examples, the operations of block 830 may be performed by the pharmacy account manager as described with reference to FIGS. 4 and 5.

At block 835, the computing device may transmit a refill completion notification (e.g., a text or a push notification indicating completion of the refill order) to the mobile device as described herein with reference to FIGS. 1 through 7. In certain examples, the operations of block 835 may be performed by the refill notification manager as described with reference to FIGS. 4 and 5.

Figure 9:
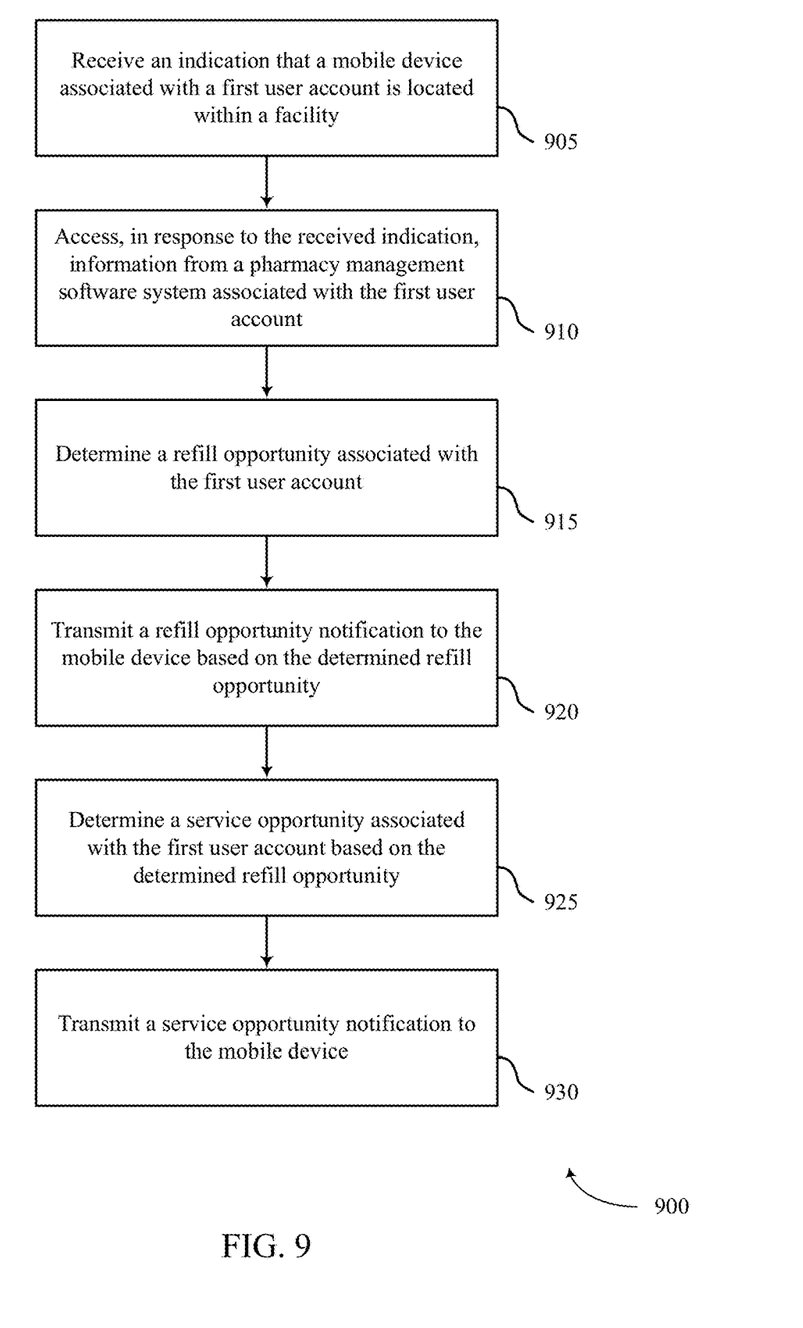

FIG. 9 shows a flowchart illustrating a method 900 for providing proximity-based pharmacy application services in accordance with various aspects of the present disclosure. The operations of method 900 may be implemented by a computing device (e.g., a server) such as pharmacy application services server 300, pharmacy application services server 400, pharmacy application services server 500, pharmacy application services server 600, or the one or more pharmacy application services servers 110 or its components as described with reference to FIGS. 1 through 6. In some examples, the computing device may execute a set of codes to control the functional elements of the computing device to perform the functions described below. Additionally or alternatively, the computing device may perform aspects the functions described below using special-purpose hardware.

At block 905, the computing device may receive an indication that a mobile device associated with a first user account is located within a facility as described herein with reference to FIGS. 1 through 8. In certain examples, the operations of block 905 may be performed by the proximity indication manager as described with reference to FIGS. 4 and 5.

At block 910, the computing device may access, in response to the received indication, information from a pharmacy management software system associated with the first user account as described herein with reference to FIGS. 1 through 8. In certain examples, the operations of block 910 may be performed by the pharmacy account manager as described with reference to FIGS. 4 and 5.

At block 915, the computing device may determine a refill opportunity associated with the first user account as described herein with reference to FIGS. 1 through 8. In certain examples, the operations of block 915 may be performed by the refill determination manager as described with reference to FIGS. 4 and 5.

At block 920, the computing device may transmit a refill opportunity notification to the mobile device based on the determined refill opportunity as described herein with reference to FIGS. 1 through 8. In certain examples, the operations of block 920 may be performed by the refill notification manager as described with reference to FIGS. 4 and 5.

At block 925, the computing device may determine a service opportunity associated with the first user account based on the determined refill opportunity as described herein with reference to FIGS. 1 through 8. In certain examples, the operations of block 925 may be performed by the service opportunity determination manager as described with reference to FIGS. 4 and 5.

At block 930, the computing device may transmit a service opportunity notification to the mobile device as described herein with reference to FIGS. 1 through 8. In certain examples, the operations of block 930 may be performed by the service opportunity determination manager as described with reference to FIGS. 4 and 5.

Alternatively or additionally in the blocks of methods 700, 800, and/or 900, the computing device may initiate an auto-payment process (e.g., payment via the mobile device and quick pick up at the pharmacy station) based on the received refill opportunity. The computing device may determine that the first user account qualifies for a medication therapy service (e.g., one or more services that may optimize therapeutic outcomes for the user such as, but not limited to, pharmacotherapy consults, anticoagulation management, immunizations, health and/or wellness programs). The determination of the medication therapy service may be based on the accessed information from the pharmacy management software system. The computing device may determine a disease state (e.g., the Flu, common could, high blood pressure, pain management, etc.) associated with the first user account based on the determined refill opportunity.

It should be noted that these methods describe possible implementation, and that the operations and the steps may be rearranged or otherwise modified such that other implementations are possible. In some examples, aspects from two or more of the methods may be combined. For example, aspects of each of the methods may include steps or aspects of the other methods, or other steps or techniques described herein. Thus, aspects of the disclosure may provide for consumer preference and maintenance interface.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described herein can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more") indicates an inclusive list such that, for example, a list of at least one of A, B, or C means A or B or C or AB or AC or BC or ABC (i.e., A and B and C).

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable read only memory (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

Thus, aspects of the disclosure may provide for techniques for contacting consumers using a consumer preference and maintenance interface. It should be noted that these methods describe possible implementations, and that the operations and the steps may be rearranged or otherwise modified such that other implementations are possible. In some examples, aspects from two or more of the methods may be combined.

The various illustrative blocks and modules described in connection with the disclosure herein may be implemented or performed with a general-purpose processor, a digital signal processor (DSP), an ASIC, an field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration). The functions of each unit may also be implemented, in whole or in part, with instructions embodied in a memory, formatted to be executed by one or more general or application-specific processors.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

What is claimed is:

1. A method of consumer interaction comprising:
   receiving, by a computing device, an indication that a mobile device associated with a first user account is located within a facility, the received indication being based at least in part on a communication associated with the mobile device and a wireless device located within or proximal to the facility;
   accessing, by the computing device in response to the received indication, information from a pharmacy management software system associated with the first user account;
   determining, by the computing device, that a refill opportunity associated with the first user account is available on an existing prescription and has not been acted upon by a user of the first user account, the determining being based at least in part on the information from the pharmacy management software system;
   determining, by the computing device, that the refill opportunity is capable of being fulfilled by the facility; and
   transmitting, by the computing device, a refill opportunity notification to the mobile device based at least in part on the determining that the refill opportunity is available on an existing prescription and has not been acted upon by a user of the first user account and the determining that the refill opportunity is capable of being fulfilled by the facility.

2. The method of claim 1, wherein determining the refill opportunity associated with the first user account comprises determining that a second user account has an available refill on an existing prescription and has not been acted upon by a user of the second user account, the second user account being linked to the first user account.

3. The method of claim 1, further comprising:
   receiving, by the computing device, a refill indication associated with the refill opportunity notification;
   initiating processing associated with the refill opportunity based at least in part on the received refill indication; and
   providing for display order information associated with at least one of the refill indication or the refill opportunity, the order information being for display to at least one device different from the mobile device.

4. The method of claim 3, further comprising:
transmitting, by the computing device, a refill completion notification to the mobile device.

5. The method of claim 3, further comprising:
initiating an auto-payment process based at least in part on the received refill indication.

6. The method of claim 1, further comprising:
determining that the first user account qualifies for a medication therapy service based at least in part on the accessed information from the pharmacy management software system.

7. The method of claim 1, further comprising:
determining a disease state associated with the first user account based at least in part on the refill opportunity;
performing, by the computing device, an authentication process based at least in part on the determining the disease state; and
transmitting, by the computing device, a healthcare opportunity notification associated with the disease state to the mobile device based at least in part on the authentication process.

8. The method of claim 1, further comprising:
determining, by the computing device and based at least in part on the information from the pharmacy management software system, that a service opportunity is available from the facility and that the service opportunity is associated with the first user account; and
transmitting, by the computing device, a service opportunity notification to the mobile device.

9. An apparatus for consumer interaction, comprising:
a processor;
memory in electronic communication with the processor; and
instructions stored in the memory and operable, when executed by the processor, to cause the apparatus to:
receive an indication that a mobile device associated with a first user account is located within a facility, the received indication being based at least in part on a communication associated with the mobile device and a wireless device located within or proximal to the facility;
access, in response to the received indication, information from a pharmacy management software system associated with the first user account;
determine that a refill opportunity associated with the first user account is available on an existing prescription and has not been acted upon by a user of the first user account, the determining being based at least in part on the information from the pharmacy management software system;
determine that the refill opportunity is capable of being fulfilled by the facility; and
transmit a refill opportunity notification to the mobile device based at least in part on determining that the refill opportunity is available on an existing prescription and has not been acted upon by a user of the first user account and determining that the refill opportunity is capable of being fulfilled by the facility.

10. The apparatus of claim 9, wherein the instructions are operable to cause the processor to:
determine the refill opportunity associated with the first user account comprises determining that a second user account has an available refill on an existing prescription and has not been acted upon by a user of the second user account, the second user account being linked to the first user account.

11. The apparatus of claim 9, wherein the instructions are operable to cause the processor to:
receive a refill indication associated with the refill opportunity notification;
initiate processing associated with the refill opportunity based at least in part on the received refill indication; and
provide for display order information associated with at least one of the refill indication or the refill opportunity, the order information being for display to at least one device different from the mobile device.

12. The apparatus of claim 11, wherein the instructions are operable to cause the processor to:
transmit a refill completion notification to the mobile device.

13. The apparatus of claim 11, wherein the instructions are operable to cause the processor to:
initiate an auto-payment process based at least in part on the received refill indication.

14. The apparatus of claim 9, wherein the instructions are operable to cause the processor to:
determine that the first user account qualifies for a medication therapy service based at least in part on the accessed information from the pharmacy management software system.

15. The apparatus of claim 9, wherein the instructions are operable to cause the processor to:
determine a disease state associated with the first user account based at least in part on the determined refill opportunity;
perform an authentication process based at least in part on determining the disease state; and
transmit a healthcare opportunity notification associated with the disease state to the mobile device based at least in part on the authentication process.

16. The apparatus of claim 9, wherein the instructions are operable to cause the processor to:
determine, based at least in part on the information from the pharmacy management software system, that a service opportunity is available from the facility and that the service opportunity is associated with the first user account; and
transmit a service opportunity notification to the mobile device.

17. A non-transitory computer-readable medium storing code for consumer interaction, the code comprising instructions executable to:
receive an indication that a mobile device associated with a first user account is located within a facility, the received indication being based at least in part on a communication associated with the mobile device and a wireless device located within or proximal to the facility;
access, in response to the received indication, information from a pharmacy management software system associated with the first user account;
determine that a refill opportunity associated with the first user account is available on an existing prescription and has not been acted upon by a user of the first user account, the determining being based at least in part on the information from the pharmacy management software system;
determine that the refill opportunity is capable of being fulfilled by the facility; and
transmit a refill opportunity notification to the mobile device based at least in part on determining that the refill opportunity is available on an existing prescription and has not been acted upon by a user of the first user account and determining that the refill opportunity is capable of being fulfilled by the facility.

18. The non-transitory computer-readable medium of claim 17, wherein the instructions are executable to:
receive a refill indication associated with the refill opportunity notification;
initiate processing associated with the refill opportunity based at least in part on the received refill indication; and
provide for display order information associated with at least one of the refill indication or the refill opportunity, the order information being for display to at least one device different from the mobile device.

* * * * *